US006649615B2

(12) United States Patent
Dubuisson et al.

(10) Patent No.: US 6,649,615 B2
(45) Date of Patent: Nov. 18, 2003

(54) METHOD FOR INHIBITING FIBROGENESIS

(75) Inventors: Liliane Dubuisson, Talence (FR);
Alexis Desmouliere, Bordeaux (FR);
Jean Rosenbaum, Bordeaux (FR)

(73) Assignee: Institute National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 10/128,995

(22) Filed: Apr. 23, 2002

(65) Prior Publication Data
US 2003/0199518 A1 Oct. 23, 2003

(51) Int. Cl.[7] .............................................. A61K 31/496
(52) U.S. Cl. ................................................. 514/252.17
(58) Field of Search ..................................... 514/252.17

(56) References Cited

U.S. PATENT DOCUMENTS 5,250,286 A * 10/1993 Skupin ......................... 424/45
6,174,917 B1 * 1/2001 McLean ..................... 514/509

OTHER PUBLICATIONS

Calo et al., Clinical Nephrology, 58(2), 103–110 (Aug., 2002).*
Albino–Teixeira A, et al., Effects of Sympathetic Denervation on Liver Fibroblasts: Prevention by Adenosine. J Auton Pharmacol 1990; 10: 181–189.
Athari A, et al., F2 Alpha and D2 Release from Primary Ito Cell Cultures after Stimulation with Noradrenaline and ATP but Not Adenosine. Hepatology 1994; 20: 142–148.
Beno DW, et al., Administration of Prostaglandin E1 Analog Reduces Rat Hepatic and Ito Cell Collagen Gene Expression and Collagen Accumulation after Bile Duct Ligation Injury. Hepatology 1993; 17: 707–714.
Bièche I, et al., Quantitation of hTERT Gene Expression in Sporadic Breast Tumors with a Real–time Reverse Transcription–polymerase Chain Reaction Assay. Clinical Cancer Research 2000; 6: 452–459.
Chomczynski P, et al., Single–step method of RNA, Isolation by Acid Guanidinium Thiocyanate–Phenol–chloroform Extraction. Anal Biochem 1987; 162: 156–159.
Faouzi S, et al., Myofibroblasts Are Responsible for Collagen Synthesis in the Stroma of Human Hepatocellular Carcinoma: an in Vivo and in Vitro Study. J Hepatol 1999; 30: 275–284.
Fort P, et al., Various Rat Adult Tissues Express Only One Major mRNA Species from the Glyceraldehyde–3–phosphate–dehydrogenase Multigenic Family. Nucleic Acids Res 1985; 13: 1431–1442.

Friedman SL., Molecular Regulation of Hepatic Fibrosis, an Integrated Cellular Response to Tissue Injury. J Biol Chem 2000; 275: 2247–2250.
Fukuda Y, et al.., Demonstration of Noradrenaline–immunoreactive Nerve Fibres in the Liver. J Int Med Res 1996; 24: 466–472.
Genovese C, et al.., Construction of DNA Sequences Complementary to Rat Alpha 1 and Alpha 2 Collagen mRNA and Their Use in Studying the Regulation of Type I Collagen Synthesis by 1,25–dihydroxyvitamin D. Biochemistry 1984; 23: 6210–6216.
Hsu CT., the Role of the Sympathetic Nervous System in Promoting Liver Cirrhosis Induced by Carbon Tetrachloride, Using the Essential Hypertensive Animal (SHR). J Auton Nerv Syst 1992; 37: 163–173.
Hsu CT., the Role of the Autonomic Nervous System in Chemically–induced Liver Damage and Repair—using the Essential Hypertensive Animal Model (SHR). J Auton Nerv Syst 1995; 51: 135–142.
Mallat A, et al., Growth Inhibitory Properties of Endothelin–1 in Activated Human Hepatic Stellate Cells: a Cyclic Adenosine Monophosphate–mediated Pathway. Inhibition of Both Extracellular Signal–regulated Kinase and c–Jun Kinase and Upregulation of Endothelin B Receptors. J Clin Invest 1996; 98: 2271–2278.
Martin C. Michel, et al., Naunyn–Schmiedeberg's Arch. Pharmacol. (1995) 352:1–10.
Stephen J. Meltzer, et al., an Improvement of the Single–step Method of RNA Isolation by Acid Guanidinium Thiocyanate–phenol–chloroform Extraction. Biotechniques 1990; 8: 148–149.
Liliane Dubuisson, et al., Inhibition of Rat Liver Fibrogenesis Through Noradrenergic Antagonism, Hepatology 2002; 35: 325–331.
Smedes F, et al., Simple and Fast Solvent Extraction System for Selective and Quantitative Isolation of Adrenaline, Noradrenaline and Dopamine from Plasma and Urine. J Chromatogr 1982; 231: 25–39.
Tuchweber B, et al., Proliferation and Phenotypic Modulation of Portal Fibroblasts in the Early Stages of Cholestatic Fibrosis in the Rat. Lab Invest 1996; 74: 265–278.
Vogel S, et al., An Immortalized Rat Liver Stellate Cell Line (HSC–T6): a New Cell Model for the Study of Retinoid Metabolism in Vitro. J Lipid Res 2000; 41: 882–893.

* cited by examiner

Primary Examiner—Phyllis G. Spivack
(74) Attorney, Agent, or Firm—Darby & Darby

(57) ABSTRACT

The present invention relates to a method for inhibiting hepatic fibrogenesis, especially liver fibrogenesis, which method comprises administering an effective amount of an alpha-adrenergic receptor antagonist to a patient in need of such treatment.

5 Claims, 2 Drawing Sheets

METHOD FOR INHIBITING FIBROGENESIS

The present invention relates to a method for inhibiting fibrogenesis, especially liver fibrogenesis, by administering an adrenergic receptor antagonist.

TECHNICAL BACKGROUND

Liver fibrosis is characterized by an excessive deposition of extracellular matrix components in the liver. Several liver cell types participate in matrix deposition, the major types being hepatic stellate cells (HSC) (Friedman et al., 2000) and portal fibroblasts (Tuchweber et al., 1996). During the past decade, a lot of attention has been given to the stimuli responsible for fibrogenic cell activation in the liver. The major focus has been on growth factors and oxidant stress (Friedman et al., 2000). Despite the fact that it is well known that the liver receives an adrenergic innervation (Hsu et al., 1992—Fukuda et al., 1996), only a few studies have focused on the role of this innervation and/or that of secreted catecholamines on liver fibrogenesis. Thus, selective adrenergic denervation with the toxic 6-hydroxydopamine (OHDA) leads to an increase in the number of portal fibroblasts in the dog and in the rabbit (Albino-Teixeira et al., 1990). Furthermore, isolated HSC respond to norepinephrin by increasing their secretion of prostaglandins (Athari et al., 1994). Prostaglandins decrease the proliferation of activated HSC (Mallat et al., 1996) and prostaglandin El treatment decreases liver fibrosis in the bile duct ligation model (Beno et al., 1993). However, it was reported that fibrosis following carbon tetrachloride ($CCl_4$) treatment is much more severe in spontaneously hypertensive rats (SHR strain) that exhibit increased concentrations of plasma catecholamines, as compared to control non hypertensive rats (Hsu et al., 1992—Hsu et al., 1995). This article did not however provide quantitative assessment of liver fibrosis.

On the other hand, alpha-adrenergic blocking agents such as prazosin were proposed in the treatment of liver diseases for their vasodilator properties (U.S. Pat. No. 6,174,917).

There was thus a need to clarify the role of the liver adrenergic innervation and catecholamines on the liver fibrogenic process.

SUMMARY OF THE INVENTION

By investigating the effects of noradrenergic antagonism on liver fibrosis, the inventors have shown that treatment with the adrenergic receptor antagonist prazosin strikingly attenuated liver fibrosis by inhibiting liver fibrogenesis.

The invention thus provides a method for inhibiting fibrogenesis, especially liver fibrogenesis, which method comprises administering an effective amount of an adrenergic receptor antagonist to a patient in need of such treatment.

In a particular embodiment, the antagonist prevents the development of liver fibrosis, especially in course of a viral hepatitis, such as chronic hepatitis C.

The adrenergic receptor antagonist may be an antagonist of alpha-1 adrenergic receptor, e.g. prazosin.

BRIEF DESCRIPTION OF THE DRAWINGS:

FIG. 1B—rat treated with $CCl_4$ and prazosin. Scale bar: 200 $\mu$m

DETAILED DESCRIPTION OF THE INVENTION

Figure 1:
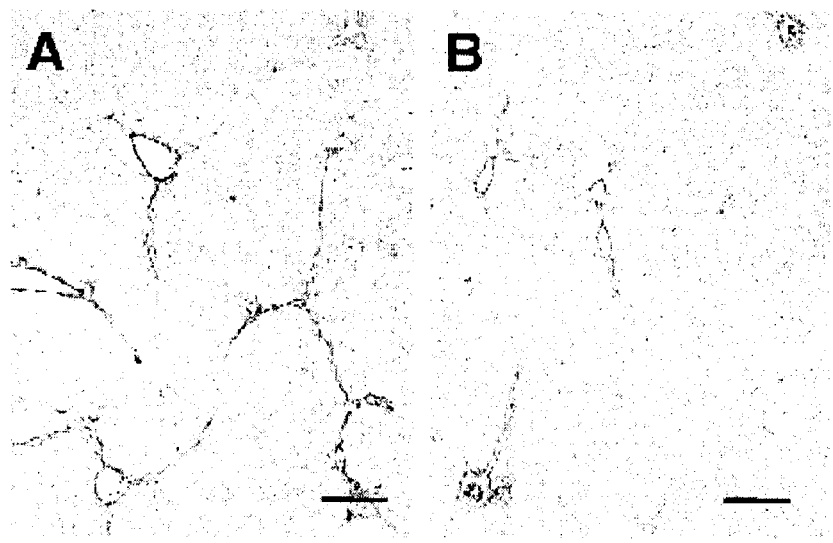
FIG. 1: Effect of prazosin treatment on liver fibrosis after $CCl_4$ (carbon tetrachloride) treatment for 2 weeks (Sirius red staining) FIG. 1A—rat treated with $CCl_4$ alone.

The inventors first investigated the effects of noradrenergic antagonism on carbon tetrachloride ($CCl_4$)—induced liver fibrosis in rats. Two weeks of $CCl_4$, induced a 5 fold increase in the area of fibrosis as compared with controls. Addition of 6-hydroxydopamine (OHDA), a toxin that destroys noradrenergic fibers, decreased fibrosis by 60%. After 6 weeks of $CCl_4$, the area of fibrosis increased about 30 fold in $CCl_4$-treated animals and was decreased by 36% with OHDA. At 2 weeks, OHDA abrogated the $CCl_4$-induced increase in mRNA level of tissue inhibitor of matrix metalloproteinases-1, an inhibitor of extracellular matrix degradation, and it greatly reduced it at 6 weeks. Prazosin, a specific alpha-1 adrenergic antagonist, was able to completely reproduce the effects of chemical sympathectomy. Indeed, when rats treated with $CCl_4$ for 2 weeks also received prazosin, fibrosis was decreased by 83%. These results show that destruction of noradrenergic fibers or antagonism of noradrenergic signaling through alpha-1 receptors inhibits the development of liver fibrosis. This also indicates that the detrimental effects of catecholamines are mainly mediated through alpha-1 receptors.

In light of these results and taking into account the fact that adrenergic receptor antagonists have a very good safety profile, the inventors contemplate using such adrenergic receptor antagonists as drugs against fibrogenesis, especially liver fibrogenesis.

Liver fibrogenesis is the active process leading to the deposition of an excess of extracellular matrix components in the liver. It is observed in a number of conditions such as chronic viral hepatitis B and C, alcoholic liver disease, drug-induced liver disease, hemochromatosis, auto-immune hepatitis, Wilson disease, primary biliary cirrhosis, sclerosing cholangitis, liver schistosomiasis and others. Fibrogenesis can occur similarly in other organs, such as lung, kidney, pancreas, heart and skin.

The method of the invention is particularly helpful in the treatment of liver fibrosis. "Liver fibrosis" is the established excess deposit of extracellular matrix components in the liver. Its endpoint is liver cirrhosis.

In a preferred aspect of the invention, the antagonist is useful to prevent the development of liver fibrosis that may occur in a patient infected by Hepatitis virus, e.g. hepatitis B virus (HBV), or hepatitis C (HCV) virus.

Chronic viral hepatitis are more particularly aimed at, especially chronic hepatitis C.

By the term "patients in need of such treatment" is meant any human subject or mammals, including sheep, cattle, dogs, cats, rodents, rabbits or goats, who suffer from an organ disease wherein fibrogenesis is observed or generally results from the development of the disease.

The terms "treatment" and "prevention" include therapy and prophylaxis toward fibrogenesis, at any stage of development of the phenomenon or before it occurs.

The invention especially aims at preventing, or reducing or alleviating liver fibrosis in patients suffering from an organ disease.

The use of therapeutically effective amounts of an alpha-adrenergic receptor antagonist in accordance with the invention effectively reduces or prevents the development of liver fibrosis.

In the context of the present invention, the alpha-adrenergic receptor antagonist may be specific of a particular subtype of alpha-adrenergic receptor or not. Specific antagonists, such alpha-1 receptor antagonists, are yet preferred. Subtypes of adrenergic receptors are described in greater detail below.

Adrenergic Receptors

Adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors.

Subsequently, the functional distinction between alpha and beta receptors was further refined by the pharmacological characterization of these receptors from various animal and tissue sources. As a result, alpha and beta adrenergic receptors were farther subdivided into $\alpha 1$, $\alpha 2$, $\beta 1$, and $\beta 2$ subtypes. Functional differences between $\alpha 1$ and $\alpha 2$ receptors have been recognized, and compounds which exhibit selective binding between these two subtypes have been developed.

For a general background on the alpha adrenergic receptors, the reader's attention is directed to Robert et al., 1991, wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. For a review of the classification of alpha 1 adrenoceptor subtypes, see, Martin et al., (1995).

Alpha-adrenergic Receptor Antagonists

Alpha-adrenergic receptor antagonists are also called adrenoreceptor antagonists, alpha-adrenergic antagonists or alpha blockers.

Examples of alpha-adrenergic receptor antagonists include prazosin whose chemical name is 1-(4-amino-6,7-dimethoxy-2-quinazolinyl)-4-(2-furanylcarbonyl) piperazine, as described in U.S. Pat. No. 3,511,836, and available under the trade name MINIPRESS (Pfizer), doxazocin whose chemical name is 1-(4-amino-6,7-dimethoxy-2-quinazolinyl)-4-[(2,3-dihydro-1,4-benzodioxin-2-yl) carbonyl]-piperazine, as described in U.S. Pat. No. 4,188,390 and available under the trade name CARDURAN (Pfizer), as well as phenoxybenzamine, phentolamine, betahistine, ergotamine, sumatripton, terazosin, bunazosin, indoramin, and alfuzosin.

Any other compounds that exhibit an antagonist activity toward alpha-adrenergic receptors are encompassed. This includes compounds under development and new compounds to be identified, and whose pharmacological behaviour can be easily characterized. Binding assays to determine the affinity and specificity of a test compound for a receptor are well-known by one skilled in the art.

Pharmaceutical Compositions

The adrenergic receptor antagonists are formulated as pharmaceutical compositions useful for inhibition of fibrogenesis, especially liver fibrogenesis.

For this purpose, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Pharmaceutical compositions containing an adrenergic receptor antagonist alone or in combination with another adrenergic receptor antagonist or another active ingredient may thus be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono-or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0, 100, 250 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As a typical example, prazosin may be administered in the form of tablets, at a daily dose of 0.3 to 1 mg.

Adrenergic receptor antagonists may be used alone at appropriate dosages defined by routine testing in order to obtain optimal antagonism of the adrenergic receptor while minimizing any potential toxicity. In addition, co-administration or sequential administration of other agents including agents aimed at either the etiological treatment of the liver disease such as antiviral agents, corticosteroids or others, or other potential antifibrotic drugs including anti-oxidants, pentoxifylline, silymarin and others.

The Examples given below illustrate the invention without restricting its scope in any way.

EXAMPLES

Example 1

Inhibition of Rat Liver Fibrogenesis Through Noradrenergic Antagonism

Material And Methods

Animals and experimental design

All experiments were carried out using accepted ethical guidelines. Male Wistar rats (Charles River, St Aubin-les-Elbeuf, France) weighing 200–250 g were used in this study. The animals had free access to food and drinking water. Fibrosis was induced by giving $CCl_4$ (Sigma, St Quentin-Fallavier, France) mixed with olive oil (1vol: 5vol.) at 0.375 ml/kg body weight by gavage, three times a week, on Monday, Wednesday and Friday. Control animals for $CCl_4$ received only olive oil.

Sympathetic chemical denervation was performed with OHDA (Sigma). OHDA was freshly prepared in saline containing 0.4% (w/v) ascorbic acid (Sigma). OHDA was administered intraperitoneally, twice a week on 2 consecutive days (Monday and Tuesday) at the dose of 25 mg/kg body weight. The first injection was given 4 to 6 hours before the first administration of $CCl_4$. Control animals for OHDA received only the solvent.

Thus, 4 groups including each 6 animals could be distinguished. Group I: olive oil and saline alone; group II: olive oil and OHDA alone; group III: $CCl_4$ with saline; group IV: $CCl_4$ with OHDA. These animals were treated for 2 weeks. In another series of experiments, animals were similarly treated for 6 weeks. In that case, both control groups included only 3 animals.

Finally, other animals were treated with the specific α1-adrenergic receptor antagonist prazosin (Sigma), given in drinking water daily at a dose of 50 mg/l during 2 weeks. Group V animals received $CCl_4$ alone, while group VI received $CCl_4$ with prazosin. Both groups included 6 animals.

At the designated time points, the animals were sacrificed. Liver samples were taken from several lobes and either snap frozen in liquid nitrogen, cryopreserved in OCT compound (Sakura, Torrance, Calif.) and snap-frozen in liquid nitrogen-cooled isopentane, or fixed in buffered formalin.

Serum samples were also collected.

Catecholamine Content

Extraction was performed on liver homogenates (10% w/v, in 0.05 M ice-cold Tris-HCl buffer at pH 7.4) according to the method of Smedes et al. using dihydroxynorepinephrine as internal standard (Smedes et al., 1982). Extracts were analyzed by HPLC with electrochemical detection.

Liver Function Tests

Routine liver function blood tests (bilirubin, alkaline phosphatase and transaminases) were performed on an automated analyzer.

Fibrosis Assessment

This was done on formalin-fixed, paraffin-embedded sections stained with Picro Sirius red, using image analysis. All samples from a series of experiments were stained simultaneously. Quantitative data were obtained using a computerized image analysis system (Biocom 500, Les Ulis, France) including a personal computer (DESK PRO, Compaq, Houston, Tex.), a CCD video camera (Sony, Japan) and a Zeiss microscope (Jena, Germany). Sampling corresponded to 3 sections from 3 different lobes. The analysis was performed on an average of 50 fields per section using the ×4 objective. The whole surface of the sections was used for analysis with the exception of large centrolobular veins (diameter $\geq 150$ μm) and large portal tracts. Fibrosis deposition was expressed as a percentage of stained areas on the total measured area.

Interassay variation was calculated in preliminary experiments and found to be 1.4%. When the percentage of reduction in areas of fibrosis consecutive to treatments was calculated, control values were first substracted.

In Situ Hybridization

In situ hybridization was performed on frozen sections according to a protocol described earlier, using [$\alpha^{33}$P]UTP labeled riboprobes (Faouzi et al., 1999). The probe used was a 900 bp fragment of the rat α2(I) collagen cDNA, (Genovese et aL, 1984). The cDNA was subcloned into the pGEM5Z f(+) vector. Antisense and sense probes were generated by in vitro transcription. Their size was reduced to ~250 nt by alkaline hydrolysis.

Quantitation of Type I Collagen Transcripts by Quantitative RT-PCR

Total RNA was prepared from liver samples by the method of Chomczynski and Sacchi (1987), modified as described by Puissant and Houdebine (1990).

Type I collagen specific transcripts were quantified by a technique of quantitative RT-PCR, that has previously been described in detail (Bieche et al., 2000). Each sample was normalized on the basis of its expression of the RPLPO gene (also known as 36B4, encoding human acidic ribosomal phosphoprotein P0).

Detection of Tissue Inhibitor of Matrix Metalloproteinases-1 (TIMP-1) Transcripts by Northern Blot Twenty pg of total RNA extracted from rat liver was analyzed by Northern blot. RNAs were separated on a 0.8% agarose gel containing ethidium bromide in MOPS buffer. Running buffer and gel contained 0.2 M formaldehyde. The RNAs were transferred onto a positively charged nylon membrane (Amersham, Orsay, France) by downward capillary transfer in running buffer. Examination of the stained membrane under UV light was used to confirm the quality of loading and transfer. A rat TIMP-1 cDNA probe was labeled with [$\alpha^{32}$P]dCTP by random priming using the Ready-to-go kit from Roche (Meylan, France). Hybridization was performed using the Ultrahyb solution (Ambion, Austin, Tex.). The blots were washed in stringent conditions (0.1×SSC, 0.1% SDS at 65° C.). To further confirm the loading and transfer accuracy, blots were rehybridized with a rat GAPDH cDNA probe (Fort et al., 1985). The signals were quantified with the Kodak 1 D Image Analysis Software (Eastman Kodak Company, Rochester, N.Y.). Results are presented as TIMP-1/GAPDH ratios.

Statistical Analysis

All values are expressed as mean ±SD. Comparison of multiple means was performed by ANOVA using the Statview 2.0 software (Abacus Concepts Inc., Berkeley, Calif.).

Results

As expected, $CCl_4$ treatment for 2 weeks induced a significant fibrosis that developed around centrolobular veins. The area of fibrosis increased from 0.63±0.06% of field area in control animals that received only olive oil (group I) to 2.86±0.78% in animals treated with $CCl_4$ (group III). Chemical denervation with OHDA effectively depleted liver norepinephrin stores as estimated by a decrease in the norepinephrin content of 87.6 or 87.4% in $CCl_4$-treated or non treated animals, respectively (Table 1).

TABLE 1

Norepinephrin content in livers of rats treated or not with $CCl_4$ and/or OHDA for 2 weeks

| Treatment | N | Norepinephrin |
|---|---|---|
| Saline (group I) | 6 | 47.6 ± 9.9 |
| OHDA alone (group II) | 6 | 6.0 ± 3.2* |
| $CCl_4$ alone (group III) | 5 | 29.1 ± 10.6 |
| $CCl_4$ + OHDA (group IV) | 6 | 3.6 ± 1.5** |

The results are expressed in ng/g of wet liver tissue as means ± 1 SD.
n = number of animals used
*statistically different from group I (p<0,000002)
** statistically different from group III (p<0,0002)

Treatment with OHDA together with $CCl_4$ (group IV) resulted in a reduction in the area of fibrosis by 60.2%, down to 1.54±0.29%. Treatment with OHDA alone (group II) had no effect by itself (fibrosis area=0.61±0.08%). These results were highly significant (p=0.0001 by ANOVA). Vital parameters and biochemical tests of liver function are presented in Table 2.

TABLE 2

Vital parameters and liver functions tests in rats after 2 weeks of $CCl_4$ treatment with or without OHDA

| Parameter | Saline (group I) (n = 6) | OHDA alone (group II) (n = 6) | $CCl_4$ alone (group III) (n = 6) | $CCl_4$ with OHDA (group IV) (n = 6) |
|---|---|---|---|---|
| Body weight (g) | 344 ± 17 | 365 ± 14 | 298 ± 12 | 293 ± 6 |
| Liver weight (g) | 12.9 ± 1.0 | 16.0 ± 1.1 | 13.7 ± 1.7 | 12.5 ± 1.0 |
| LW/BW ratio (X100) | 3.7 ± 0.2 | 4.4 ± 0.2 | 4.6 ± 0.7 | 4.1 ± 0.6 |
| ASAT (IU.I$^{-1}$) | 120 ± 9 | 94 ± 18 | 173 ± 82 | 137 ± 29 |
| ALAT (IU.I$^{-1}$) | 43 ± 4 | 50 ± 6 | 130 ± 98 | 97 ± 37 |
| Alkaline phosphatase (IU.I$^{-1}$) | 178 ± 48 | 274 ± 46 | 276 ± 53 | 225 ± 58 |
| Bilirubin ($\mu$M.I$^{-1}$) | 4.5 ± 1.4 | 2.3 ± 0.5 | 3.2 ± 0.7 | 5.0 ± 1.4 |

Results were expressed as means ±1SD. No difference was statistically significant.

Although there was a trend towards lower values of serum ASAT, ALAT and alkaline phosphatase in animals receiving OHDA with $CCl_4$ (group IV) as opposed to $CCl_4$ alone (group III), the differences failed to reach statistical significance.

No gross toxic effects of the prolonged OHDA treatment could be detected in control animals (group II). To the contrary, OHDA-treated animals exhibited a significantly higher body weight as compared to untreated rats (p=0.047). They also had larger livers (p=0.0006), liver/body weight ratios (p=0.0002) and higher serum alkaline phosphatase values (p=0.005) (Table 2). However, the histologic aspect of the livers from these animals was strictly normal.

As the toxicity of $CCl_4$ depends on the initial induction of hepatocyte necrosis, the authors of the invention examined the possibility that OHDA acted by decreasing the toxicity of $CCl_4$. Thus, groups of animals treated with 2 administrations of $CCl_4$ with or without 2 injections of OHDA were sacrificed 24 hours after the second $CCl_4$ treatment and evaluated for acute toxicity of $CCl_4$ by serum tests and measurement of the area of necrosis on liver sections. The data are presented in Table 3. There was no statistically significant difference between the 2 groups.

TABLE 3

Liver functions tests and area of necrosis in rats after 96 hs of $CCl_4$ treatment with or without OHDA

| Treatment | Bilirubin IU.I$^{-1}$ | Alkaline phosphatase IU.I$^{-1}$ | ASAT IU.I$^{-1}$ | ALAT IU.I$^{-1}$ | Necrosis area % |
|---|---|---|---|---|---|
| $CCl_4$ (n = 9) | 6.0 ± 1.7 | 314 ± 111 | 452 ± 152 | 269 ± 117 | 4.6 ± 2.3 |
| $CCl_4$+ OHDA (n = 6) | 5.2 ± 1.5 | 240 ± 117 | 342 ± 62 | 221 ± 71 | 3.3 ± 1.0 |

The percentage of necrosis area was determined on hematoxylin and eosin stained sections by image analysis.

Results were expressed as mean ±1SD. No difference was statistically significant.

In order to verify that the beneficial effect of OHDA was also observed in a model of more severe fibrosis, rats were treated with $CCl_4$ for 6 weeks with or without OHDA. This regimen resulted in severe fibrosis with septa formation. Six Weeks OHDA alone had no effect on the area of fibrosis (0.47±0.03%) compared to untreated controls. However, it decreased the effect of $CCl_4$ by 36% (12.38±1.89 vs 18.82±1.79%, p=0.0001). The decrease in fibrosis area was accompanied by a reduction in type I collagen mRNA level: as determined by quantitative RT-PCR, a 6 weeks treatment with $CCl_4$ increased collagen mRNA level from 16.0±5.9 to 477.2±91.0 arbitrary units. When animals received $CCl_4$ together with OHDA, collagen mRNA level was 364.5±68.7, thus decreased by 24% as compared with animals receiving only $CCl_4$ (p=0.01 by ANOVA).

OHDA treatment results in depletion of noradrenergic fibers. The inventors reasoned that norepinephrin receptor antagonists should reproduce its effect. The inventors chose to use the selective α1 adrenergic receptor antagonist prazosin. When rats were intoxicated for 2 weeks with $CCl_4$, the concurrent administration of prazosin strikingly reduced the extent of fibrosis (FIG. 1). Histomorphometry showed a decrease in fibrosis area by 83%, from 2.35±0.41% to 0.89±0.21% (p=0.0001). In situ hybridization for type I collagen transcripts clearly demonstrated a large decrease in transcripts when animals were treated with prazosin. As for OHDA, prazosin treatment did not decrease the acute toxicity of $CCl_4$, as checked by biological tests and necrosis area measurement (Table 4). In that case, most values tended to be higher in the prazosin-treated group although the differences were not statistically significant.

TABLE 4

Liver functions tests and area of necrosis in rats after 2 weeks of $CCl_4$ treatment with or without prazosin

| Treatment | Bilirubin $IU.l^{-1}$ | Alkaline phosphatase $IU.l^{-1}$ | ASAT $IU.l^{-1}$ | ALAT $IU.l^{-1}$ | Necrosis area % |
|---|---|---|---|---|---|
| $CCl_4$ (n = 6) | 5.0 ± 0.8 | 262 ± 56 | 445 ± 264 | 245 ± 216 | 5.6 ± 2.0 |
| $CCl_4$ + prazosin (n = 6) | 4.8 ± 0.9 | 258 ± 64 | 576 ± 161 | 298 ± 156 | 6.6 ± 2.3 |

The percentage of necrosis area was determined on hematoxylin and eosin stained sections by image analysis.

Results were expressed as mean ±1SD. No difference was statistically significant.

Figure 2:
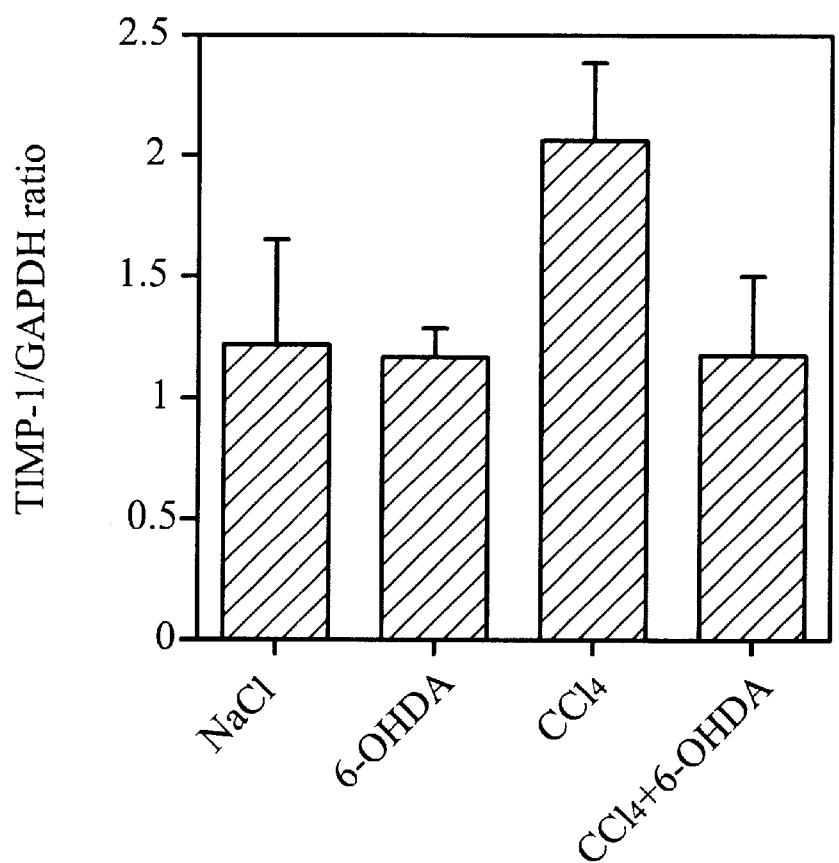
FIG. 2: Effect of OHDA (6-hydroxydopamine) treatment on hepatic TIMP-1 (tissue inhibitor of matrix metalloproteinases-1) mRNA levels Twenty pg total RNA was extracted from the livers of rats treated for 2 weeks as indicated and was analyzed by Northern blot with a rat TIMP-1 probe. The blot was then stripped and rehybridized with a rat GAPDH (glyceraldehyde-3-phosphate dehydrogenase) probe. The figure shows the quantitation of TIMP-1/GAPDH ratios, expressed as mean ±1 SD.

Fibrosis deposition results from an imbalance between synthesis and degradation of its components. During liver fibrosis, failure of degradation has been consistently associated to an upregulation of the matrix metalloproteinase inhibitor TIMP-1. The inventors thus evaluated the levels of TIMP-1 mRNA by Northern blot in our experimental conditions. As shown on FIG. 2, expression of TIMP-1 mRNA was increased in animals treated with $CCl_4$ for 2 weeks (group III), as compared to both control groups (I and II) that exhibited similar values. Co-administration of OHDA (group IV) resulted in a normalization of the TIMP-1/GAPDH ratio back to control values (p=0.001, Student's t test). An overall 45% reduction in the ratio was also seen at 6 weeks but the difference failed to reach statistical significance due to a single animal in the OHDA group with a very high value. When this animal was removed from the analysis, the decrease reached 57% and was significant (p=0.05).

Example 2

The Adrenergic Pathway in Fibrogenesis

To elucidate the action of alpha-adrenergic antagonists in fibrogenesis, the inventors have first examined the effect of norepinephrin on hepatic stellate cell proliferation and expression of tissue inhibitor of metalloproteinases-1.

Material and Methods
Cells

The inventors used an established rat HSC cell line, named HSC-T6. These cells have been extensively characterized and exhibit many similarities with primary cultures of HSC (Vogel et al, 2000).

Cell Proliferation Assay

Cells were exposed to increasing concentrations of norepinephrin for 2 days. In some experiments, cells were also exposed to increasing concentrations of prazosin. Cell number was evaluated through the measurement of the reduction of the dye 3-(4,5-dimethylthiazol-2yl)-2,5 diphenyltetrazolium.

Expression of Tissue Inhibitor of Matrix Metalloproteinases-1 (TIMP-1) mRNA

TIMP-1 increases fibrosis deposition by inhibiting its degradation by matrix metalloproteinases. The inventors observed in example 1 that noradrenergic antagonism in vivo led to a drastic decrease in liver TIMP-1 mRNA expression. They have further measured the effect of norepinephrin on TIMP-1 mRNA expression by cultured HSC-T6 cells. Total RNA was purified from cells exposed for 3, 6, or 24 hours to 100 nM norepinephrin. The RNAs were analyzed by Northern blot with a probe specific for rat TIMP-1. The blots were subsequently dehybridized and rehybridized with a probe to rat glyceraldehyde 3-phosphate dehydrogenase to ensure proper loading and transfer. TIMP-1/GADPH ratios were calculated and the results are shown respective to control values without norepinephrin.

Results
Proliferation

Figure 3:
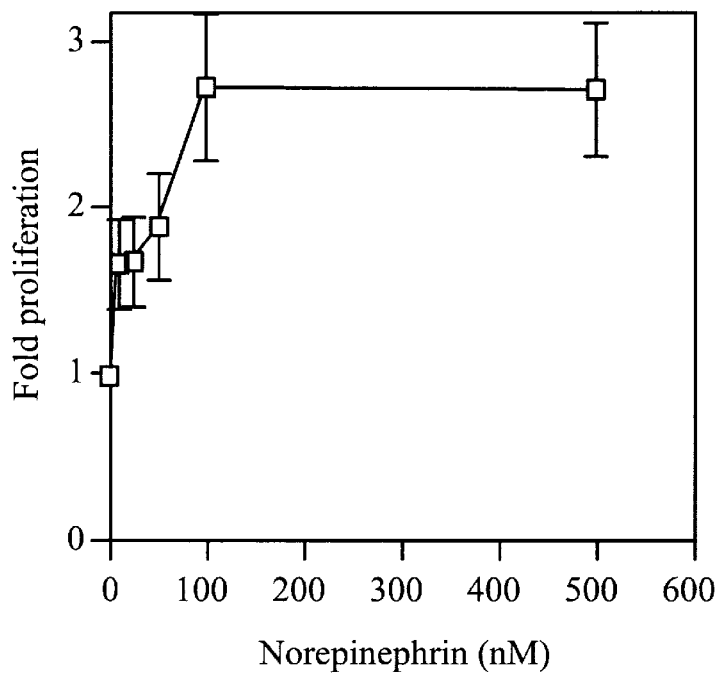
FIG. 3: Effect of norepinephrin on hepatic stellate cell (HSC) proliferation. Cells were exposed to increasing concentrations of norepinephrin for 2 days. Cell number was evaluated through the measurement of the reduction of the dye 3-(4,5-dimethylthiazol-2yl)-2,5 diphenyltetrazolium.

As shown on FIG. 3, norepinephrin dose-dependently increased HSC-T6 proliferation with a plateau at 100 nM. Half-maximal effect was seen at 25 nM. The results show the mean value from 5 independent experiments conducted in triplicate.

Figure 4:
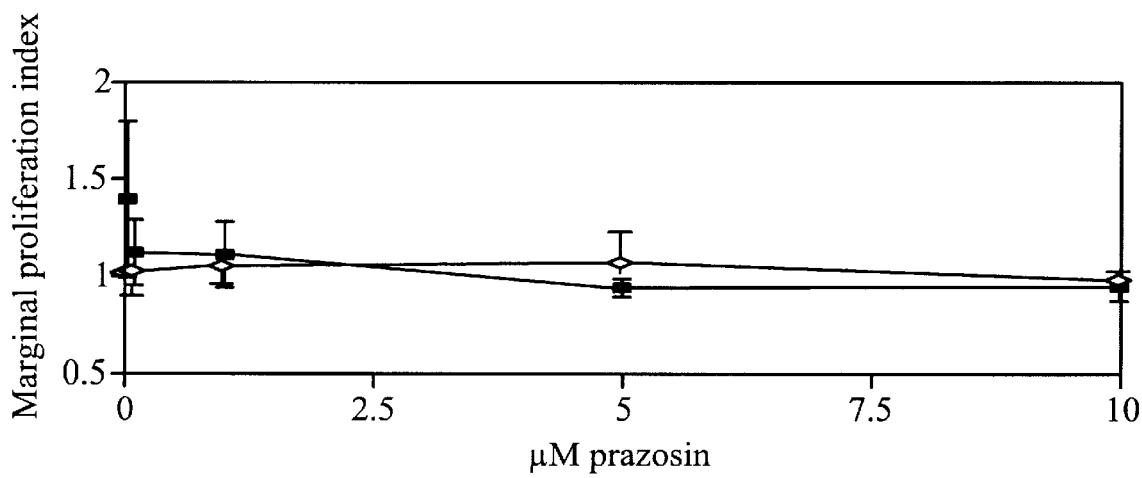
FIG. 4: Effect of prazosin on hepatic stellate cell proliferation induced by norepinephrin Cells were exposed to increasing concentrations of prazosin, either alone (open symbols), or in the presence of 100 nM norepinephrin (closed symbols). Cell number was evaluated through the measurement of the reduction of the dye 3-(4,5-dimethylthiazol-2yl)-2,5 diphenyltetrazolium. The marginal proliferation index was calculated as: $(OD_{experimental\ sample} - OD_{day\ 0})/(OD_{control} - OD_{day\ 0})$, where OD is the optical density measured at the end of the experiment.

As shown on FIG. 4, the mitogenic effect of norepinephrin (100 nM) on HSCT-6 was abolished by simultaneous addition of prazosin. Prazosin alone had no effect. The results show the mean value from 3 independent experiments conducted in quadruplicate.

TIMP-1

A shown in Table 5, 100 nM norepinephrin increased TIMP-1 expression at the 3 time points studied. The effect was statistically significant at the 6 hour time point. The effect of norepinephrin was close to that of transforming growth factor β1 (TGFβ1), a major agonist of liver fibrogenesis. The results are the mean of 4 to 5 independent experiments.

TABLE 5

Effect of norepinephrin or TGFβ1 on TIMP-1 expression

| Time (h) | Norepinephrin 100 nM | TGFβ1 0,1 ng/ml |
|---|---|---|
| 3(n = 4) | 1,30 ± 0,15 | 1,56 ± 0,20 |
| 6(n = 4) | 1,38 ± 0,13 | 1,38 ± 0,11 |
| 24(n = 5) | 1,15 ± 0,18 | 1,33 ± 0,09 |

Results are expressed as TIMP-1/GAPDH ratios relative to control values (mean ±SEM)

Conclusion

These data demonstrate that norepinephrin directly increases 2 hallmarks of liver fibrogenesis, namely proliferation and TIMP-1 expression. It is thus likely that at least part of the beneficial effects of noradrenergic antagonism are consecutive to its effect on stellate cells.

Example 3

Reduction of Liver Fibrosis Progression in Patients Infected With Hepatitis C

Despite therapeutic improvements, liver fibrosis remains a major problem for patients infected with hepatitis C virus.

Progression of fibrosis may lead to cirrhosis that is responsible for a high morbidity and mortality. A therapeutic trial is designed where patients infected with HCV receive the up-to-date anti-viral regimen combined or not with an alpha-1 adrenergic blocker.

This is a multicenter randomized trial against placebo. Patients with proven HCV infection are included if they have significant fibrosis (METAVIR F3 or F4) and no contra-indications to the use of the proposed therapy.

Patients receive the anti-viral therapy (a combination of PEG-ylated interferon alpha and ribavirin) together with the alpha-1 adrenergic blocker or placebo for 1 year. The anti-viral treatment is then discontinued and the alpha-1 adrenergic blocker or placebo is given for an additional year before evaluation of the results.

The main endpoint of the study is the progression of liver fibrosis as assessed by histomorphometrical analysis of pre- and post-therapeutic liver biopsies.

REFERENCES

Albino-Teixeira A, Matias A, Soares-da-Silva P, Sarmento A, Azevedo I. Effects of sympathetic denervation on liver fibroblasts: prevention by adenosine. J Auton Pharmacol 1990; 10: 181–189.

Athari A, Hanecke K, Jungermann K. Prostaglandin F2 alpha and D2 release from primary Ito cell cultures after stimulation with noradrenaline and ATP but not adenosine. Hepatology 1994; 20: 142–148.

Beno D W, Espinal R, Edelstein B M, Davis B H. Administration of prostaglandin E1 analog reduces rat hepatic and Ito cell collagen gene expression and collagen accumulation after bile duct ligation injury. Hepatology 1993; 17: 707–714.

Bieche I, Nogues C, Paradis V, Olivi M, Bedossa P, Lidereau R, Vidaud M. Quantitation of hTERT gene expression in sporadic breast tumors with a real-time reverse transcription-polymerase chain reaction assay. Clinical Cancer Research 2000; 6: 452–459.

Chomczynski P, Sacchi N. Single-step method of RNA isolation by acid guanidinium thiocyanate-phenol-chloroform extraction. Anal Biochem 1987; 162: 156–159.

Faouzi S, Le Bail B, Neaud V, Boussarie L, Saric J, Bioulac-Sage P, Balabaud C, et al. Myofibroblasts are responsible for collagen synthesis in the stroma of human hepatocellular carcinoma: an in vivo and in vitro study. J Hepatol 1999; 30: 275–284.

Fort P, Marty L, Piechaczyk M, el Sabrouty S, Dani C, Jeanteur P, Blanchard JM. Various rat adult tissues express only one major mRNA species from the glyceraldehyde-3-phosphate-dehydrogenase multigenic family. Nucleic Acids Res 1985; 13: 1431–1442.

Friedman SL. Molecular regulation of hepatic fibrosis, an integrated cellular response to tissue injury. J Biol Chem 2000; 275: 2247–2250.

Fukuda Y, Imoto M, Koyama Y, Miyazawa Y, Hayakawa T. Demonstration of noradrenaline-immunoreactive nerve fibres in the liver. J Int Med Res 1996; 24: 466–472.

Genovese C, Rowe D, Kream B. Construction of DNA sequences complementary to rat alpha 1 and alpha 2 collagen mRNA and their use in studying the regulation of type I collagen synthesis by 1,25-dihydroxyvitamin D. Biochemistry 1984; 23: 6210–6216.

Hsu CT. The role of the sympathetic nervous system in promoting liver cirrhosis induced by carbon tetrachloride, using the essential hypertensive animal (SHR). J Auton Nerv Syst 1992; 37: 163–173.

Hsu CT. The role of the autonomic nervous system in chemically-induced liver damage and repair—using the essential hypertensive animal model (SHR). J Auton Nerv Syst 1995; 51: 135–142.

Mallat A, Préaux A M, Serradeil-Le Gal C, Raufaste D, Gallois C, Brenner D A, Bradham C, et al. Growth inhibitory properties of endothelin-1 in activated human hepatic stellate cells: a cyclic adenosine monophosphate-mediated pathway. Inhibition of both extracellular signal-regulated kinase and c-Jun kinase and upregulation of endothelin B receptors. J Clin Invest 1996; 98: 2771–2778.

Martin C. Michel, et al., Naunyn-Schmiedeberg's Arch. Phanmacol. (1995) 352:1–10.

Puissant C, Houdebine L M. An improvement of the single-step method of RNA isolation by acid guanidinium thiocyanate-phenol-chloroform extraction. Biotechniques 1990; 8: 148–149.

Robert R. Ruffolo, Jr., Adrenoreceptors: Molecular Biology. Biochemistry and Pharmacology, (Progress in Basic and Clinical Pharmacology series, Karger, 1991)

Smedes F, Kraak J C, Poppe H. Simple and fast solvent extraction system for selective and quantitative isolation of adrenaline, noradrenaline and dopamine from plasma and urine. J Chromatogr 1982; 231: 25–39.

Tuchweber B, Desmouliere A, Bochaton-Piallat M L, Rubbia-Brandt L, Gabbiani G. Proliferation and phenotypic modulation of portal fibroblasts in the early stages of cholestatic fibrosis in the rat. Lab Invest 1996; 74: 265–278.

Vogel S, Piantedosi R, Frank J, Lalazar A, Rockey D C, Friedman S L, Blaner W S. An immortalized rat liver stellate cell line (HSC-T6): a new cell model for the study of retinoid metabolism in vitro. J Lipid Res 2000; 41: 882–893.

What is claimed is:

1. A method for inhibiting hepatic fibrogenesis, which method comprises administering an effective amount of an alpha-adrenergic receptor antagonist to a patient in need of such treatment.

2. The method according to claim 1, wherein the antagonist prevents the development of liver fibrosis in the course of viral hepatitis.

3. The method according to claim 1, wherein the antagonist prevents the development of liver fibrosis in the course of chronic hepatitis C.

4. The method according to claim 1, wherein the antagonist is an antagonist of alpha-1 adrenergic receptor.

5. The method according to claim 1, wherein the antagonist is prazosin.

* * * * *

UNITED STATES PATENT AND TRADEMARK OFFICE
CERTIFICATE OF CORRECTION

PATENT NO. : 6,649,615 B2
DATED : November 18, 2003
INVENTOR(S) : Liliane Dubuisson et al.

It is certified that error appears in the above-identified patent and that said Letters Patent is hereby corrected as shown below:

<u>Title page,</u>
Item [73], Assignee, please delete "Institute National de la Sante et de la Recherche Medicale (INSERM)" and substitute -- Institut National de la Sante et de la Recherche Medicale (INSERM) --.

Signed and Sealed this

Twenty-third Day of March, 2004

JON W. DUDAS
*Acting Director of the United States Patent and Trademark Office*